US005443459A

United States Patent [19]

Wong et al.

[11] Patent Number: 5,443,459
[45] Date of Patent: Aug. 22, 1995

[54] OSMOTIC DEVICE FOR DELAYED DELIVERY OF AGENT

[75] Inventors: Patrick S. L. Wong, Palo Alto; Felix Theeuwes, Los Altos Hills; Steven D. Larsen, Dublin; Liang C. Dong, Mountain View, all of Calif.

[73] Assignee: Alza Corporation, Palo Alto, Calif.

[21] Appl. No.: 109,120

[22] Filed: Aug. 19, 1993

Related U.S. Application Data

[63] Continuation-in-part of Ser. No. 830,160, Jan. 31, 1992, Pat. No. 5,312,388, which is a continuation-in-part of Ser. No. 648,270, Jan. 30, 1991, abandoned, and a continuation-in-part of Ser. No. 871,465, Apr. 20, 1992, which is a continuation-in-part of Ser. No. 745,822, Aug. 16, 1991, abandoned, which is a continuation-in-part of Ser. No. 648,270, Jan. 30, 1991, abandoned.

[51] Int. Cl.$^6$ ............................................. A61K 9/22
[52] U.S. Cl. ........................................ 604/892.1
[58] Field of Search ............. 604/892.1, 891.1, 131, 604/141, 151; 424/438, 457

[56] References Cited

U.S. PATENT DOCUMENTS

| | | | |
|---|---|---|---|
| 3,732,865 | 5/1973 | Higuchi et al. | 128/260 |
| 3,845,770 | 11/1974 | Theeuwes et al. | 128/260 |
| 3,865,108 | 2/1975 | Hartop | 128/260 |
| 3,916,899 | 11/1975 | Theeuwes et al. | 128/260 |
| 3,995,631 | 12/1976 | Higuchi et al. | 128/260 |
| 4,002,173 | 1/1977 | Manning et al. | 128/296 |
| 4,034,756 | 7/1977 | Higuchi et al. | 128/260 |
| 4,063,064 | 12/1977 | Saunderss et al. | 219/121 L |
| 4,088,864 | 5/1978 | Theeuwes et al. | 219/121 LM |
| 4,111,202 | 9/1978 | Theeuwes | 128/260 |
| 4,200,098 | 4/1980 | Ayer et al. | 128/260 |
| 4,207,893 | 6/1980 | Michaels | 128/260 |
| 4,265,874 | 5/1981 | Bonsen et al. | 424/15 |
| 4,285,987 | 8/1981 | Ayer et al. | 427/3 |
| 4,320,759 | 3/1982 | Theeuwes | 128/260 |
| 4,327,725 | 5/1982 | Cortese et al. | 128/260 |
| 4,449,983 | 5/1984 | Cortese et al. | 604/892 |
| 4,455,143 | 6/1984 | Theeuwes et al. | 604/892.1 |
| 4,526,938 | 7/1985 | Churchill et al. | 525/415 |
| 4,595,583 | 6/1986 | Eckenhoff et al. | 424/15 |
| 4,601,896 | 7/1986 | Nugent | 4424/36 |
| 4,612,008 | 9/1986 | Wong et al. | 604/892 |
| 4,643,731 | 2/1987 | Eckenhoff | 604/892 |
| 4,663,148 | 5/1987 | Eckenhoff et al. | 424/454 |
| 4,692,433 | 9/1987 | Hostetler et al. | 514/12 |
| 4,874,388 | 10/1989 | Wong et al. | 604/891.1 |
| 5,017,381 | 5/1991 | Maruyama et al. | 424/472 |
| 5,023,088 | 6/1991 | Wong et al. | 424/473 |

FOREIGN PATENT DOCUMENTS

| | | | |
|---|---|---|---|
| 0384642 | 8/1990 | European Pat. Off. | A61K 9/22 |
| WO9009168 | 8/1990 | WIPO | A61K 9/22 |
| WO9009169 | 8/1990 | WIPO | A61K 9/22 |

OTHER PUBLICATIONS

Liew et al., "Cross-protection in mice infected with influenza A virus by the respiratory route is correlated with local IgA antibody rather than serum antibody or cytotoxic T cell reactivity", Eur. J. Immunol., 1984, vol. 14, pp. 350–356.

(List continued on next page.)

*Primary Examiner*—C. Fred Rosenbaum
*Assistant Examiner*—Manuel Mendez
*Attorney, Agent, or Firm*—Felissa H. Cagan; Steven F. Stone; Edward L. Mandell

[57] ABSTRACT

The present invention is directed to a fluid-imbibing dispensing device for the initially delayed delivery of an active agent to a fluid environment of use and to a method of using the dispensing device. The dispenser comprises a housing having a first wall section and a second wall section in reversibly sliding telescopic arrangement with each other, which housing maintains its integrity in the environment of use; an internal compartment surrounded and defined by the housing; at least one active agent formulation in the compartment; and expansion means and a push plate in the compartment for separating apart the first and second wall sections of the housing after exposure to the environment of use to expose the active agent formulation to the environment of use.

1 Claim, 6 Drawing Sheets

OTHER PUBLICATIONS

Renegar et al., "Immunoglobulin A Mediation of Murine Nasal Anti-Influenza Virus Immunity", Journal of Virology, Apr. 1991, vol. 65, No. 4, pp. 2146–2148.

Renegar et al., "Passive Transfer off Local Immunity to Influenza Virus Infection by IgA Antibody", The Journal of Immunology, vol. 146, pp. 1972–1978, No. 6 Mar. 15, 1991.

Waldman et al., "Secretory Antibody Following Oral Influenza Immunization", The American Journal of the Medical Sciences, Dec. 1986, vol. 292, No. 6, pp. 367–371.

Murphy et al., "The Systemic and Mucosal Immune Response of Humans to Influenza A Virus", Current Topics in Microbiology and Immunology, vol. 146, pp. 107–116.

OSMOTIC DEVICE FOR DELAYED DELIVERY OF AGENT

This application is a continuation-in-part of U.S. application Ser. No. 07/830,160, filed Jan. 31, 1992 and now U.S. Pat. No. 5,312,388, which is a continuation-in-part of U.S. application Ser. No. 07/648,270, filed Jan. 30, 1991, now abandoned; and this application is also a continuation-in-part of U.S. application Ser. No. 07/871,465, filed Apr. 20, 1992, which is a continuation-in-part of U.S. application Ser. No. 07/745,822, filed Aug. 16, 1991, now abandoned, which is a continuation-in-part of U.S. application Ser. No. 07/648,270, filed Jan. 30, 1991, now abandoned.

FIELD OF THE INVENTION

The present invention is related to the delayed delivery of an active agent. More particularly, it is related to osmotically-activated devices for dispensing active agents to a biological environment of use following an initial delay.

BACKGROUND OF THE INVENTION

Osmotic dispensing devices for delivery of therapeutically active agents are well known in the art. Such devices use an expansion means to deliver an agent to an environment of use over a period of hours, days or months. The expansion means absorbs liquid, expands, and acts to drive out beneficial agent formulation from the interior of the device in a controlled, usually constant manner. The osmotic expansion means is used to controllably, usually relatively slowly, and over a period of time, deliver the agent. Thus, these devices are not generally used to delay the initial release of the agent, followed by the rapid release, or substantially simultaneous introduction, of all of the agent or all of the dosage form(s) containing the agent into the environment of use at one time.

The delay of the initial release of an agent has primarily been previously effected by coating the agent or a formulation containing the agent with a dissolvable or bioerodible coating layer, such as gelatin, which coating dissolves or erodes in the environment of use to then make the agent available. Delayed initial release has also been provided by dispersing the agent in a dissolvable or erodible matrix. However, such systems are often unreliable and release cannot be controlled with great accuracy due to the variability and relatively uncontrollable nature of erosion and dissolution.

PCT publication WO 90/09168 discloses an oral delivery capsule having two pieces, one of which is a plug made of a water-sensitive material. A delay in the initial release of an agent is provided by the plug taking up water, resulting in the plug swelling or expanding and eventually separating from the body of the capsule to allow release of the agent contained within. Unfortunately, the swelling and eventual release of the plug causes the volume inside the capsule to expand, which creates a vacuum within the capsule that causes fluid from the fluid environment to enter the capsule and come into contact with the active agent. When the active agent is sensitive to fluids, as are certain proteins and peptides, such contact can cause agglomeration or inactivation of the agent. Additionally, the fluid taken up by the swelling water-sensitive plug also can come into contact with fluid-sensitive active agents.

Therefore, there remains a continuing need for improved methods and systems for providing a delayed initial delivery of an active agent to an environment of use that are reliable and that can be programmed to deliver the agent after a particular interval with increased accuracy and while protecting sensitive active agents.

SUMMARY OF THE INVENTION

The present invention is directed to a fluid-imbibing dispensing device for the initially delayed delivery of an active agent to a fluid environment of use. The dispenser comprises a housing having a first wall section and a second wall section in reversibly sliding telescopic arrangement with each other, which housing maintains its integrity in the environment of use; an internal compartment surrounded and defined by the housing; at least one active agent formulation in the compartment, which formulation includes at least one active agent; and an expansion means in the compartment for separating apart the first and second wall sections of the housing after exposure to the environment of use to expose the active agent formulation to the environment of use. In a presently preferred embodiment, the device additionally comprises a partition layer or push plate between the expansion means and the open end of the first wall section.

The invention also is directed to a method for delaying the initial delivery of an active agent to a fluid environment of use, the method comprising placing the dispensing device of the invention into the environment of use, allowing fluid to be imbibed through at least a portion of the housing of the dispensing device for causing the expansion means to expand and exert pressure on the slidably connected first and second wall sections, and delivering the active agent from the dispensing device by the expansion means increasing in volume, thereby pushing apart and separating the two wall sections of the device's housing to expose the active agent formulation to the environment. During the delay period in the environment (that is, prior to the separation of the first and second wall sections), the volume of the reservoir containing the active agent is kept constant; therefore, there is a negligible pressure gradient between the environment and the interior of the reservoir. As a result, net flow of the environmental fluid driven by the pressure to enter the reservoir is minimal, so that the active agent is not contaminated or diluted.

DESCRIPTION OF THE DRAWINGS

The drawings are not drawn to scale, but are set forth to illustrate various embodiments of the invention. Like numbers refer to like structures.

DETAILED DESCRIPTION OF THE INVENTION

The present invention provides a device which is useful for the initial delayed delivery of an active agent formulation to a fluid environment of use, the delivery of the agent formulation from the dispensing device, once begun, being quickly completed rather than being continued over a prolonged period of time. By "prolonged period of time" is meant an extended time period such as for several hours, days, weeks or months. In the present invention, in contrast, the delivery device is designed to substantially simultaneously introduce all of the active agent formulation, which formulation can be either an immediate release dosage form or a controlled release dosage form, to exposure to the environment of use substantially at one time after the initial period of delay. By "substantially simultaneously introduce" and "exposure to the environment substantially at one time" are meant that all of the active agent formulation is exposed or introduced to the environment within 2 hours or less after the two wall sections of the device have separated, preferably within 1 hour or less after separation.

As used herein, the terms "therapeutically effective" amount or rate refer to the amount or rate of the active agent needed to effect the desired therapeutic, often beneficial, result.

The dispensing devices of the invention find use, for example, in humans or other animals. The environment of use is a fluid-containing environment and can comprise the stomach, the intestinal tract, or a body cavity such as the peritoneum or vagina. A single dispensing device or several dispensing devices can be administered to a subject during a therapeutic program.

Figure 1:
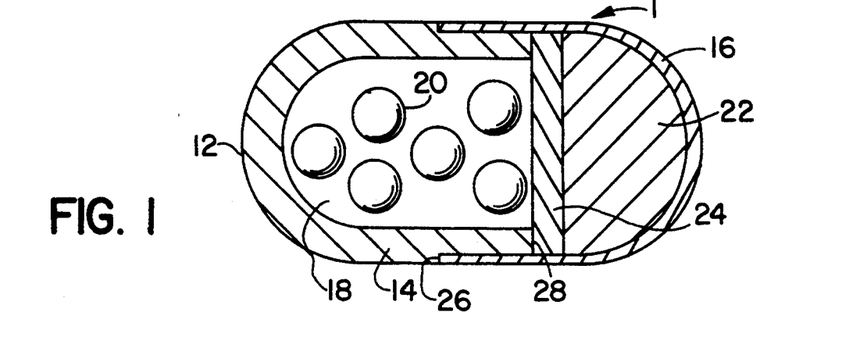
FIG. 1 is a cross-sectional view of one embodiment of the present invention, the device being in closed or prepared form prior to placement in the environment of use.

FIG. 1 depicts in cross-sectional view a presently preferred embodiment of the delivery device according to the present invention. The device is shown in closed or prepared form prior to placement in the environment of use. Dispensing device 1 comprises a housing 12 formed of a first wall section 14 and a second wall section 16. First wall section 14 and second wall section 16 are in reversibly sliding telescopic arrangement with each other. Housing 12 surrounds and defines an internal compartment 18. First wall section 14 surrounds that portion of internal compartment 18 that contains an active agent formulation, in this embodiment the formulation being a plurality of active agent dosage forms 20. Second wall section 16 surrounds that portion of internal compartment 18 that contains an expansion means 22 for expanding and for occupying space in compartment 18. Second wall section 16 also contains a partition layer or push plate 24, which layer 24 is positioned between the agent formulation 20 and the expansion means 22. Push plate 24, in a presently preferred embodiment, comprises a composition that is substantially impermeable to the passage of fluid, and it serves to restrict the passage of fluid present in the expansion means into that area of compartment 18 that contains the agent formulation. It operates to essentially maintain the integrity of the active agent formulation and the expansion means layer. Additionally, and importantly, push plate 24 acts to insure that the expanding driving force generated by the expansion means 22 is applied directly against the first wall section 14 to effect the separation of the two wall sections. Thus, push plate 24 must be of sufficient strength, thickness and rigidity to transfer the driving force against first wall section 14.

First wall section 14 has an open end with a recessed outer edge for forming receiving means 26 for slidably receiving and engaging the open end of second wall section 16. The two wall sections at their open ends are close in size and they form a friction fit therebetween. The friction generated is sufficient to maintain the two wall sections together prior to activation of the expansion means but not so great as to keep the two wall sections from sliding apart once an expanding driving force is exerted. Where additional friction is desired, protrusions or other means may be present on one or the other of the contacting surfaces of the first and second wall sections. First wall section 14 and second wall section 16 can be telescoped completely into a closed and continuous external walled position. The open end of first wall section 14 is adapted to fit within second wall section 16. The bottom edge of the open end of first wall section 14 provides a platform or ridge 28 protruding into compartment 18. Ridge 28 is adapted to receive the driving force of the expansion means 22, via the push plate 24, to effect the separation of the two wall sections.

In operation, as the expansion means 22 absorbs and imbibes fluid through second wall section 16 from the environment of use, it expands and pushes against push plate 24, causing the push plate to slide inside compartment 18. Push plate 24 moves toward and contacts ridge 28, pushing against ridge 28 and thus against first wall section 14 to cause the first wall section to slide apart from second wall section 16 as the expansion means 22 continues to expand. This causes the two wall sections to become separated and the active agent formulations 20 to be exposed to the environment of use, as illustrated in FIG. 2.

Figure 2:
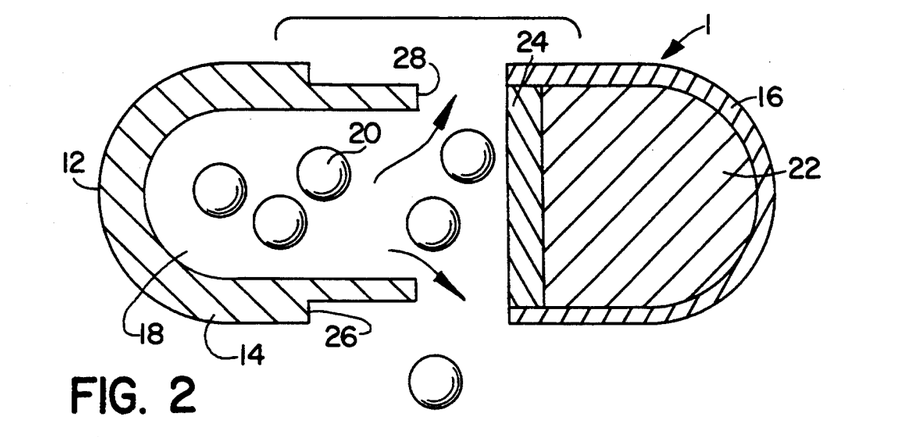
FIG. 2 is the device of FIG. 1 in operation after activation by placement in the environment of use, showing the device opened to release the active agent formulation to the environment.

FIG. 2 illustrates the dispensing device 1 of FIG. 1 in operation after activation of the device by placement in the environment of use. FIG. 2 shows device 1 opened to release all of the active agent dosage forms 20 to the environment substantially at the same time. First wall section 14 has been separated from second wall section 16 by the expanding driving force of the expansion means 22, which has expanded in size as a result of imbibing fluid from the environment. The large arrows in FIG. 2 indicate the exiting of the agent formulation dosage forms 20 from internal compartment 18 through the open end of first wall section 14, which is now in communication with the environment.

While the active agent formulation of FIGS. 1 and 2 is shown as a plurality of agent dosage forms, the active agent formulation may alternately be present as a single homogeneous or heterogeneous mass within first wall section 14 and may be in solid, liquid or semi-solid form or may comprise a thermosensitive formulation. The agent formulation may comprise a pharmaceutically acceptable carrier in addition to the active agent, with the agent being dispersed homogeneously or heterogeneously within the carrier.

First wall section 14 may comprise a composition that is semipermeable, that is, it is permeable to fluid but impermeable to active agent and other ingredients contained in dispensing device 1, or it may, alternatively, comprise a composition that is impermeable to the exchange of fluid, agent and other ingredients. When an active agent or an active agent dosage form is sensitive to fluid from an exterior fluid present in the environment of use, it is preferred that first wall section 14 be substantially impermeable to the ingress of the external fluid to serve as a means for substantially protecting the agent or dosage form until it is expelled from housing 12 and delivered into the environment of use.

Because expansion means 22 operates by the imbibition of external fluid, second wall section 16 in at least a portion that is adjacent to expansion means 22 must be semipermeable; that is, it is permeable to the passage of fluid while being substantially impermeable to the passage of other ingredients contained in dispensing device 1.

Wall sections 14 and 16 optionally comprise additional ingredients such as, for example, a plasticizer. Impermeable and semipermeable compositions suitable for use in wall sections 14 or 16, as well as suitable additives, are known in the art, examples of which are disclosed in U.S. Pat. No. 4,874,388, the entire disclosure of which is incorporated herein by reference.

Housing 12, comprising wall sections 14 and 16, is nontoxic, biologically inert, nonallergenic and nonirritating to body tissue, and it maintains its physical and chemical integrity; that is, housing 12 does not erode or degrade in the environment of use during the dispensing period. It is within the scope of the invention that the housing be insoluble only during the period of intended use and can thereafter dissolve away in the environment of the device. Thus, a dispenser is here contemplated which is unaffected by its environment, solubility-wise, at the situs of use or which, alternatively, is only slightly soluble during the period of intended use, such that once its active agent content has been removed it will then dissolve or erode away leaving no objectionable residue or empty container at the situs of use.

The expansion means or expandable driving member 22, operable for separating the first and second wall sections to release the active agent from the dispensing device of the invention, is nontoxic, nonallergenic and biologically inert. Expansion means 22 comprises, in one presently preferred embodiment, an osmopolymer. The osmopolymers interact with water and aqueous biological fluids and swell or expand to an equilibrium state. The osmopolymers exhibit the ability to swell in fluid and to retain a significant portion of the imbibed and absorbed fluid within the polymer structure. The expansion means 22 in another preferred embodiment comprises an osmagent. The osmagents are known also as osmotically effective solutes and they are also known as osmotically effective compounds. The osmagents that can be used for the purpose of this invention include inorganic and organic compounds that exhibit an osmotic pressure gradient across a semipermeable, i.e. a fluidpermeable, wall. The expansion means 22 in yet another preferred embodiment comprises an osmagent dispersed within an osmopolymer. The expansion means 22 can comprise a tablet or a layer, or a plurality of tablets or layers, or it can be pressed into second wall section 16. The osmagent or osmopolymer can be in any suitable form such as particles, crystals, pellets, granules, and the like, when pressed into a tablet layer and into wall section 16. Osmagents and osmopolymers are known to the art and are described in, for example, U.S. Pat. Nos. 3,865,108, 4,002,173, 4,207,893, 4,327,725 and 4,612,008.

Push plate 24, present in certain embodiments of the invention between the active agent formulation and the expansion means, is a means for transmitting the force generated by the expansion means against the first wall section 14, for maintaining the separate identity of the active agent formulation and the expansion means, and for substantially restricting the passage of fluid between the active agent formulation and the expansion means. Representative materials useful as a partition layer or push plate 24 are known to the art in, for example, U.S. Pat. No. 4,874,388.

The term "active agent formulation", as used herein, comprises the active agent to be delivered, as a liquid, solid, semisolid or thermosensitive composition, generally in a carrier substance and with or without additional inert ingredients. The term may additionally include dosage forms comprising the active agent which are capable of maintaining their physical configuration and chemical integrity while housed within the dispenser. These include, without limitation, tablets with or without a density element; matrix tablets; spheres; pellets and elongated tablets; capsules; tiny pills, which may be time-release; elementary osmotic pumps, such as those described in U.S. Pat. No. 3,845,770; mini-osmotic pumps, such as those described in U.S. Pat. Nos. 3,995,631, 4,034,756 and 4,111,202; and multi-chamber osmotic systems referred to as push-pull and push-melt osmotic pumps, such as those described in U.S. Pat. Nos. 4,320,759 and 4,449,983; all the above patents of which are incorporated herein by reference. In certain instances, such as when it is desired to maintain a gradient of concentration of an active agent on the epithelium surface of the gastrointestinal tract for a prolonged period of time, the dosage form can be small particles having a density greater than 1. This can be accomplished by, for example, incorporating into the particle a heavy compound such as titanium oxide or ferrous oxide, e.g. The weighted particles will penetrate the mucus layer of the GI tract and touch the epithelium cells. The mucus layer physically holds the particles on the epithelium surface, an alternative to bioadhesion.

The pharmaceutically acceptable carrier useful herein may comprise more than one ingredient, such as, for example, a buffer, a viscosity regulating vehicle, a surfactant, dyes, a permeation enhancer, proteinase inhibitors, or other formulation ingredients and additives, as are known in the art. The carrier may contain more than one active agent. The active agent formulation can erode or disintegrate and can be in the form of a wax formulation, solid core or tablet, for example. The formulation can immediately dissolve upon exposure to fluid or it may erode slowly with or without the presence of excipients for controlling erosion.

The active agent formulation can be designed in a multitude of ways to provide a specific drug delivery profile. One embodiment may comprise a formulation that contains a biologically acceptable solid surfactant which is capable of slow dispersion in the environmental fluid. In another embodiment, the formulation may contain a fluid-insoluble wax and a surfactant so that the formulation is susceptible to erosion in the environment. In still another embodiment, the formulation may be effervescent and provide drug delivery in a finely dispersed form. This is accomplished by the addition of a solid basic compound capable of evolving carbon dioxide in the presence of an acid in the environment of use. Suitable basic compounds are disclosed in U.S. Pat. No. 4,265,874. In a further embodiment, the formulation may include an osmotic agent or solute, such as those described above with reference to the expansion means 22, so that when the formulation comes into contact with the environmental fluid, it immediately dissolves. In yet another embodiment, the agent formulation can be comprised of an agent and a thermo-responsive composition. In this manner, the formulation would exhibit solid-like properties at room temperature of 21° C. and within a few degrees Celsius thereof, and would have a melting point that approximates mammalian body temperatures of 37° C. and within a few degrees Celsius thereof. The term "thermo-responsive" as used herein, in a preferred embodiment denotes the physical-chemical property of an agent carrier composition to exhibit solid, or solid-like properties at temperatures up to 31° C. and become fluid, semisolid or viscous when disturbed by heat at temperatures from 31° C., usually in the range of 31° C. to 45° C. Suitable materials useful as active agent carriers and excipients are known in the art and are disclosed in U.S. Pat. Nos. 4,595,583 and 4,874,388, for example.

The expressions "active agent" and "drug" are used interchangeably herein and in the appended claims and as used refer broadly to any agent, drug, compound, composition of matter or mixture thereof that can be delivered from the system to produce a therapeutic, beneficial or useful result or effect. This includes pesticides, herbicides, germicides, biocides, algicides, rodenticides, fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, microorganism attenuators and other agents that benefit the environment of use.

The terms "active agent" and "drug" as used here in further include any physiologically or pharmacologically active substance that produces a localized or systemic effect or effects in animals, including warm-blooded mammals, humans and primates; avians; domestic household, sport or farm animals such as dogs, sheep, goats, cattle, horses and pigs; laboratory animals such as mice, rats and guinea pigs; fish; reptiles; zoo and wild animals; and the like. The active drug which can be delivered includes inorganic and organic compounds, including, without limitation, those materials that act upon the central nervous system such as hypnotics and sedatives, psychic energizers, tranquilizers, anticonvulsants, muscle relaxants, antiparkinson agents, analgesics, anti-inflammatories, local anesthetics, muscle contractants, antimicrobials, antimalarials, hormonal agents including contraceptives, sympathomimetrics, diuretics, lipid regulating agents, antiandrogenic agents, antiparasitics, neoplastics, antineoplastics, hypoglycemics, nutritional agents and supplements, growth supplements, antienteritis agents, fats, ophthalmics, electrolytes and diagnostic agents.

Examples of beneficial agents with which this invention can be utilized include, but are not limited to, prochlorperazine edisylate, ferrous sulfate, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, aspirin, indomethacin, naproxen, fenoprofen, sulindac, indoprofen, nitroglycerin, isosorbide mononitrate, isosorbide dinitrate, propranolol, timolol, atenolol, alprenolol, cimetidine, clonidine, imipramine, colchicine, levodopa, chlorpromazine, methyldopa, dihydroxyphenylalanine, theophylline, calcium gluconate, ketoprofen, ibuprofen, cephalexin, haloperidol, zomepirac, ferrous lactate, vincamine, diazepam, phenoxybenzamine, diltiazem, milrinone, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, enalaprilat, captopril, ramipril, endlapriat, famotidine, nizatidine, sucralfate, etintidine, tetratolol, minoxidil, chlordiazepoxide, flutamide, amitriptyline, and imipramine.

This invention is particularly suited to the delivery of pharmacologically active peptides and protein anabolic hormones such as growth promoting hormones related to the endocrine system comprising, for example, porcine growth promoting hormone, bovine growth promoting hormone, equine growth promoting hormone, ovine growth promoting hormone, human growth promoting hormone, growth promoting hormones derived by extraction and concentration from pituitary and hypothalamus glands, growth promoting hormones produced by recombinant DNA methods, bovine growth promoting hormone as described in Nucleic Acid Res., Vol. 10, p 7197 (1982), ovine growth promoting hormone as described in Arch. Biochem. Biophys., Vol. 156, p 493 (1973), and porcine growth promoting hormone as described in DNA, Vol. 2, pp 37, 45 (1983). Also included are proteins and polypeptides including, but not limited to, growth hormones including human growth hormone, somatropin, somatotropin, somatomedin-C, gonadotropic releasing hormone, follicle stimulating hormone, luteinizing hormone, LHRH, growth hormone releasing factor, gonadotropin releasing factor, insulin, calcitonin, chorionic gonadotropin, oxytocin, vasopressin, adrenocorticotrophic hormone, vaccines, antibodies, antigens including influenza antigen, epidermal growth factor, fibroblast growth factor, platelet-derived growth factor, transforming growth factor, nerve growth factor, insulin-like growth factor, prolactin, somatostatin, octreotide, cosyntropin, lypressin, thyrotropic hormone, thyrotropin releasing hormone, thyroid stimulating hormone, secretin, pancreozymin, enkephalin, glucagon, renin, prolactin, corticotrophin, interleukins, interleukin receptor antagonist, interferons, superoxide dismutase, leukotriene synthesis inhibitors such as lipoxygenase inhibitors, leukotriene antagonists, parathyroid and pituitary hormones, methyltestosterone, 17-$\beta$-estradiol, ethinyl estradiol, ethinyl estradiol 3-methyl ether, prednisolone, 17-$\beta$-hydroxyprogesterone acetate, 19-nor-progesterone, norgestrel, norethindrone, norethisterone, norethiederone, progesterone, norgesterone, norethynodrel, gestodene, ST-1435, fertility inhibitors such as the prostaglandins, fertility promoters, and the like, and structurally similar bioactive equivalents thereof. By "structurally similar bioactive equivalent" is meant a polypeptide with an amino acid sequence which, although not identical to that of the naturally occurring peptide, is sufficiently similar in structure to produce substantially equivalent therapeutic effects on the subject to that produced by the natural peptide itself. As used herein and in the appended claims, the terms "protein", "peptide" and "polypeptide" refer to both the naturally occurring chemical entities and the structurally similar bioactive equivalents thereof. Other active agents useful in the practice of this invention include colon-targeting mediators of wound healing such as lactic acid or local vasodilators. The active agents and their dosage unit amounts are known to the art in The Pharmacological Basis of Therapeutics, by Gilman, Goodman, Ral7 and Murad, 7th Ed., (1985) published by MacMillan Publishing Co., N.Y.; in Pharmaceutical Sciences, Remington, 17th Ed., (1985) published by Mack Publishing Co., Easton, PA; and in U.S. Pat. No. 4,526,938.

It is to be understood that more than one active agent may be incorporated into the active agent formulation in a device of this invention, and that the use of the term "agent" or "drug" in no way excludes the use of two or more such agents or drugs.

The agents can be in a wide variety of chemical and physical forms, such as uncharged molecules, components of molecular complexes or nonirritating, pharmacologically acceptable salts. Also, simple derivatives of the agents (such as ethers, esters, amides, etc.) which are easily hydrolyzed by body pH, enzymes, etc., can be employed.

The amount of active agent employed in the delivery device will be that amount necessary to deliver a therapeutically effective amount of the agent to achieve the desired result at the site of delivery. In practice, this will vary widely depending upon the particular agent, the site of delivery, the severity of the condition, and the desired therapeutic effect. Thus, it is not practical to define a particular range for the therapeutically effective amount of active agent incorporated into the device.

Figure 3:
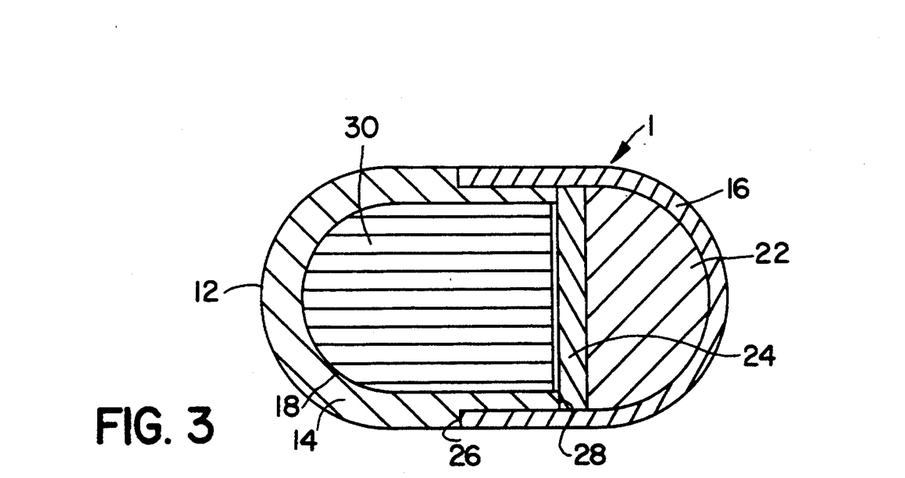
FIG. 3 is a cross-sectional view of the device of FIG. 1 but containing a different form of an active agent formulation.

FIG. 3 illustrates another embodiment of the dispensing device 1 of the present invention. As illustrated in this figure, dispensing device 1 is similar to the dispensing device of FIGS. 1 and 2, having a housing 12, a first wall section 14, a second wall section 16, an internal compartment 18 surrounded and defined by housing 12, expansion means 22, push plate 24, receiving means 26 and ridge 28, but contains an active agent formulation 30 that is of a different form than that of FIGS. 1 and 2. Active agent formulation 30 is present as a single homogeneous or heterogeneous mass and may be in solid, liquid or semi-solid form or may comprise a thermo-sensitive composition. Agent formulation 30 may comprise a pharmaceutically acceptable carrier in addition to the active agent, with the agent being dispersed homogeneously or heterogeneously within the carrier.

Figure 4:
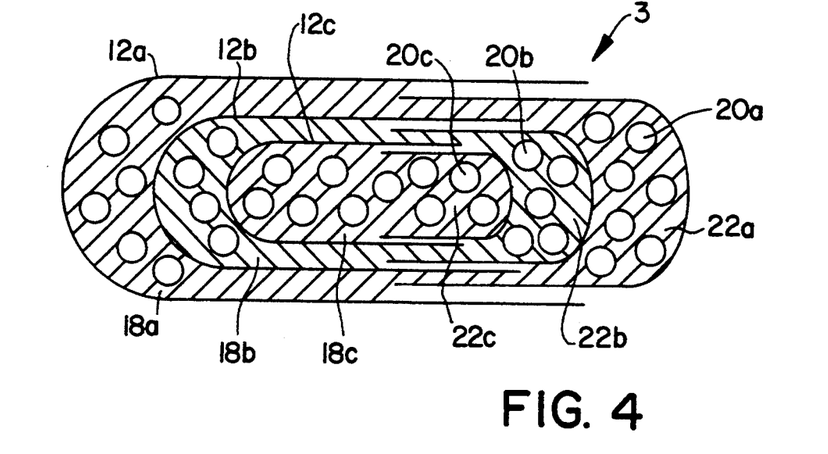
FIG. 4 is a cross-sectional view of yet another embodiment of the present invention, directed to a multi-pulse dispensing device.

A multi-pulse delivery of active agent formulation over an extended period of time, such as 24 hours, may be provided by utilizing sequentially smaller dispensing devices of the invention enclosed within each other. Such a multi-pulse dispenser is illustrated in FIG. 4. In FIG. 4, multi-pulse dispensing device 3 is comprised of a plurality of housings 12a, 12b and 12c, each smaller than the other and contained within the internal compartment of the next larger housing. Thus, housing 12c is contained within internal compartment 18b of housing 12b, and housing 12b (containing housing 12c) is itself contained within internal compartment 18a of housing 12a. Also contained within each of the compartments 18a, 18b and 18c are active agent formulation dosage forms 20a, 20b and 20c, respectively, dispersed in expansion means 22a, 22b and 22c, respectively. As housing 12a is opened by the expanding driving force of expansion means 22a, it releases housing 12b into the environment of use as it releases active agent dosage forms 20a. Housing 12b is then exposed to the environmental fluid and is opened after a delay period by the expanding driving force of expansion means 22b, releasing active agent dosage forms 20b together with housing 12c. Housing 12c in its turn is then exposed to the environmental fluid to release active agent dosage forms 20c by expansion of means 22c.

Figure 5:
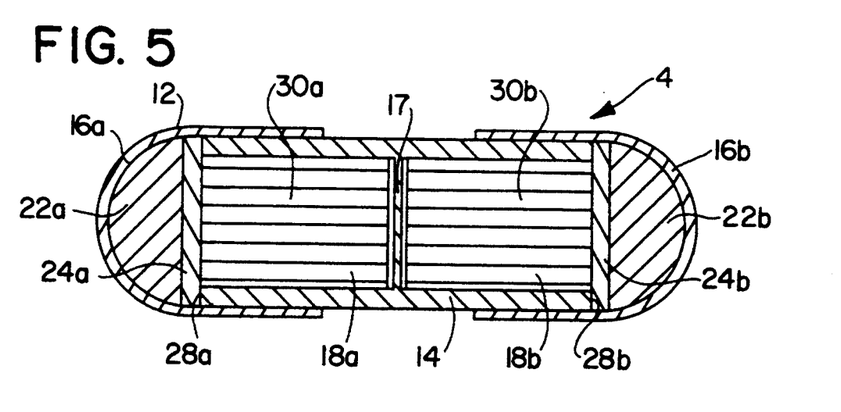
FIG. 5 is a cross-sectional view of an embodiment of the present invention directed to a multi-agent and/or multi-pulse dispensing device.
Figure 6:
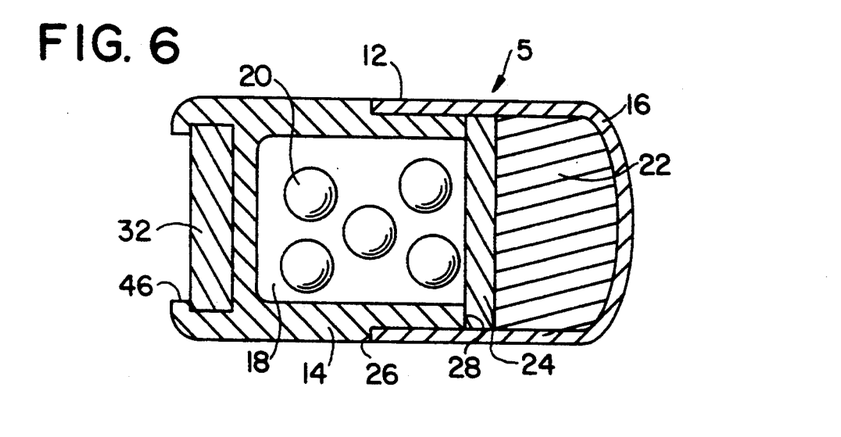
FIG. 6 is a cross-sectional view of an embodiment of the present invention which includes a loading dose for the initial rapid delivery of an agent.

FIG. 5 illustrates an embodiment of the invention where two active agents are delivered from the same device. Such a dispensing device is desirable when, for example, the agents must be kept separated because they are physically or chemically incompatible with each other or when the agents are to be delivered to the environment at different points in time. Dispensing device 4 comprises a housing 12 formed of a first wall section 14 and two second wall sections 16a and 16b. First wall section 14 has two opposing open ends and includes an impermeable internal dividing wall 17 which divides the space encompassed by housing 12 into two internal compartments 18a and 18b. That part of first wall section 14 encompassed by one of its two open ends and dividing wall 17 surrounds that portion of internal compartment 18a that contains an active agent formulation 30a. That part of first wall section 14 encompassed by the other of its two open ends and dividing wall 17 surrounds that portion of internal compartment 18b that contains an active agent formulation 30b. Formulations 30a and 30b may comprise the same active agent or different active agents. The two formulations may be the same or different; for example, they may both be liquids, or one may be solid and one liquid, or one may be a liquid and the other a plurality of dosage forms, or other combinations. Formulations 30a and 30b may comprise the same active agent but in two different chemical forms, such as the base drug and a salt of the same drug.

Second wall section 16a of dispensing device 4 surrounds that portion of internal compartment 18a that contains an expansion means 22a for expanding and for occupying space in compartment 18a. Second wall section 16a also contains a push plate 24a, which push plate 24a is positioned between the agent formulation 30a and the expansion means 22a. Second wall section 16b surrounds that portion of internal compartment 18b that contains an expansion means 22b for expanding and for occupying space in compartment 18b. Second wall section 16b also contains a push plate 24b, which push plate 24b is positioned between the agent formulation 30b and the expansion means 22b. The bottom edge of each of the open ends of first wall section 14 provides a platform or ridge 28a and 28b protruding into compartments 18a and 18b, respectively, for receiving the driving force of the expansion means via push plates 24a and 24b, respectively, to separate apart the first wall section and the second wall sections.

Where it is desired to deliver active agent formulations 30a and 30b substantially concurrently, the composition of expansion means 22a and 22b will be the same so that they will have identical expansion profiles, to separate the first wall section from both second wall sections at substantially the same time. Where it is desired, on the other hand, to deliver active agent formulations 30a and 30b at different points in time, that is, after different initial delay periods (a multi-pulse system), the composition of the two expansion means will be different in order to provide the different initial delay periods. Alternately, the composition of the semipermeable second wall sections 16a and 16b can be different from each other to provide a different rate of fluid uptake into the expansion means 22a and 22b, respectively, to provide different initial delay periods. Another embodiment of the invention is very similar to that illustrated in FIG. 5 except that it does not include an impermeable internal dividing wall 17. Thus, the delivery device of this similar embodiment (not shown) comprises a housing 12 formed of a first wall section 14 and two second wall sections 16a and 16b, expansion means 22a and 22b, push plates 24a and 24b, and ridges 28a and 28b. First wall section 14 has two opposing open ends and encompasses one internal compartment 18, which compartment 18 contains one active agent formulation 30 or a plurality of dosage forms 20. This doublecapped embodiment is useful when it is desired to expedite the release of the active agent formulation 30 or 20 from the device once the agent formulation is exposed to the environment of use. In such a use, the composition of expansion means 22a and 22b will normally be the same so that the expansion means will separate the first wall section from the two second wall sections at substantially the same time to release the active agent formulation 30 or 20.

Figure 7:
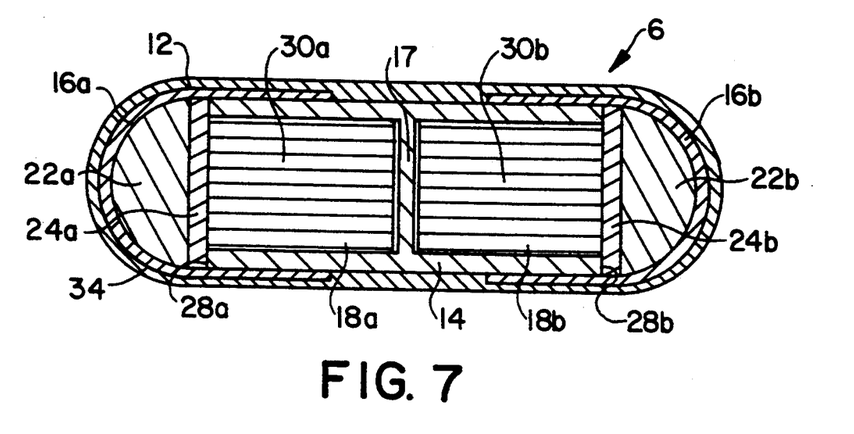
FIG. 7 is a cross-sectional view of another embodiment of the invention which includes a loading dose of agent.

It may, in certain instances, be desirable to provide an initial rapid delivery of an active agent to the environment of use in addition to the delayed delivery of active agent provided by this invention. Such initial agent delivery may be accomplished by means for providing an initial agent dose. FIG. 6 illustrates one means of initial agent delivery. In FIG. 6, dispensing device 5 comprises housing 12 having a first wall section 14 and a second wall section 16, internal compartment 18, active agent formulation dosage forms 20, expansion means 22, push plate 24, receiving means 26 and ridge 28. Dispensing device 5 additionally comprises an initial agent delivery means or loading dose 32. Loading dose 32 comprises at least one active agent homogeneously or heterogeneously dispersed or dissolved in an appropriate carrier means, which can be a solid, paste, gel, semisolid, or the like, or a thermo-sensitive material which provides a dispensable material in the environment of use. The loading dose 32 can be in the form of a tablet or capsule, for example, and can be round, spheroid, toroid, cylindrical, square, and the like. Loading dose 32 is located on or within dispensing device 5 in such a manner that, upon application of the device to the environment of use, the loading dose is immediately exposed to the environment. This may be accomplished by means of a retaining device such as a ridge (as illustrated by retaining ridge 46), a gelatin cap which dissolves, or a screen, for example. Once device 5 is placed in the environment of use, loading dose 32 dissolves, erodes, osmotically bursts or otherwise begins to dispense the active agent contained therein. At the same time, expansion means 22 will begin to imbibe fluid, expanding to begin to separate first wall section 14 and second wall section 16. This provides a pulsed or, alternatively, a continuous delivery of agent from loading dose 32 at a first time period and a pulsed delivery of agent from the agent dosage forms 20 at a second time period. The formulation of the loading dose 32 can be so designed that the delivery of the initial agent could be completed prior to the delivery of the dosage forms 20 or, alternatively, that the initial agent could provide a continuous delivery for a period up to and even after the delivery of the dosage forms. The loading dose and the agent dosage forms may contain the same active agent or different active agents.

Delivery of an initial agent dose may also be accomplished by coating housing 12 externally with an overcoat or loading dose containing an active agent, as is illustrated in FIG. 7. In FIG. 7, dispensing device 6 is the same as device 4 of FIG. 5, except that device 6 also comprises an overcoat or loading dose 34 that surrounds housing 12. Once placed in the environment of use, loading dose 34 will begin immediately to dissolve, erode or otherwise dispense an active agent contained in the loading dose. In this embodiment, the expansion means 22*a* and 22*b* of the device cannot begin to imbibe water and become activated until such time as the loading dose 34 has dissolved or eroded away from the semipermeable membranes of second wall sections 16*a* and 16*b*, so that a good portion if not all of the active agent in the loading dose will have been dispersed prior to the dispersion of the agent in active agent formulations 30*a* and/or 30*b*, thus providing a multi- (two- or three-) pulse delivery of agent.

FIGS. 8 and 9 are cross-sectional views of another embodiment of the dispensing device of the present invention, prior to delivery (FIG. 8) and subsequent to delivery (FIG. 9) of the device to an environment of use. Dispensing device 7 comprises a housing 12 formed by a first wall section 14 and a second wall section 16, the two wall sections being in reversibly sliding telescopic arrangement and enclosing an internal compartment 18. That portion of compartment 18 enclosed by first wall section 14 contains a first active agent delivery chamber and a second active agent delivery chamber and an impermeable barrier layer 40 which separates the two active agent chambers. Barrier layer 40 is preferably non-moveable in the device. The first active agent delivery chamber includes at least one first active agent formulation 36, and exit means 42 for providing communications between the active agent formulation and the environment of use, and a first expansion means 34 for dispensing the first active agent formulation 36 through the exit means 42 to the environment substantially immediately and over a prolonged period of time. In a preferred embodiment the first agent formulation 36 and the first expansion means 34 are separated by a moveable impermeable first partition layer 38 to maintain the separate identities of the first agent formulation 36 and the first expansion means 34. The second active agent delivery chamber includes at least one second active agent formulation 30 and has an open end defined by the open end of the first wall section 14.

The exit means or port may comprise one orifice or a plurality of orifices and is formed by conventional techniques described in the literature. Included among these methods are mechanical drilling, laser drilling, and liquid techniques using an orifice-forming agent, such as erosion, extraction, dissolving, bursting or leaching, depending on the nature of the agent used. The first wall section 14 will contain at least one such orifice, and in most configurations, one orifice will suffice. The dimensions of the orifice in terms of both diameter and length will affect the rate at which the drug is released from the device in response to the pressure differential resulting from the volumetric expansion of the first expansion means caused by the osmotic imbibition. The considerations involved in determining the optimum dimensions of the orifice for any particular device or drug are the same as those for orifices of osmotic devices of the prior art, and selection of the appropriate dimensions will be readily apparent to those skilled in the art.

That portion of compartment 18 enclosed by second wall section 16 contains an expansion chamber, for separating apart the first and second wall sections of the housing after exposure to the environment of use for dispensing the second active agent formulation 30 to the environment in a pulse after an initially delayed period of time. The expansion chamber includes a second expansion means 22 and a moveable impermeable second partition layer or push plate 24, push plate 24 being between second expansion means 22 and second active agent formulation 30 and positioned to come into contact with the end or ridge 28 of the open end of first wall section 14.

At least that portion of first wall section 14 adjacent to first expansion means 34 must be of a semipermeable composition, since the expansion means is activated by the imbibition of water. Likewise, second wall section 16 is of semipermeable composition. When first wall section 14 is semipermeable adjacent to second active agent formulation 30, an impermeable inner wall 44 may be present between first wall section 14 and agent formulation 30 when it is desired to protect the active agent from fluid from the environment. Such an additional impermeable wall may also be present between wall section 14 and first active agent formulation 36 when it is desired to protect the active agent in formulation 36 from fluid from the environment.

In practice, as fluid is imbibed by first expansion means 34, the expanding driving force of means 34 is conveyed via first partition layer 38 against the first active agent formulation 36, and agent formulation 36 is then immediately begun to be expelled in a controlled and continuous manner from internal compartment 18 through exit port 42 into the environment of use, providing an initial active agent dose. At the same time, second expansion means 22 begins to expand and exert a driving force via second partition layer or push plate 24 against end or ridge 28 of first wall section 14 to begin to slidably separate first wall section 14 from second wall section 16. Second agent formulation 30 is only delivered to the environment of use at the point in time ($t_b$) when first wall section 14 and second wall section 16 have separated apart from each other. In such a manner, first agent formulation 36 is continuously delivered to the environment for an extended or prolonged time ($t_a$) while a pulse of second agent formulation 30 is delivered at a later, delayed time ($t_b$). First agent formulation 36 and second agent formulation 30 may comprise the same active agent or different active agents or they may comprise the same active agent in different forms.

Figure 8:
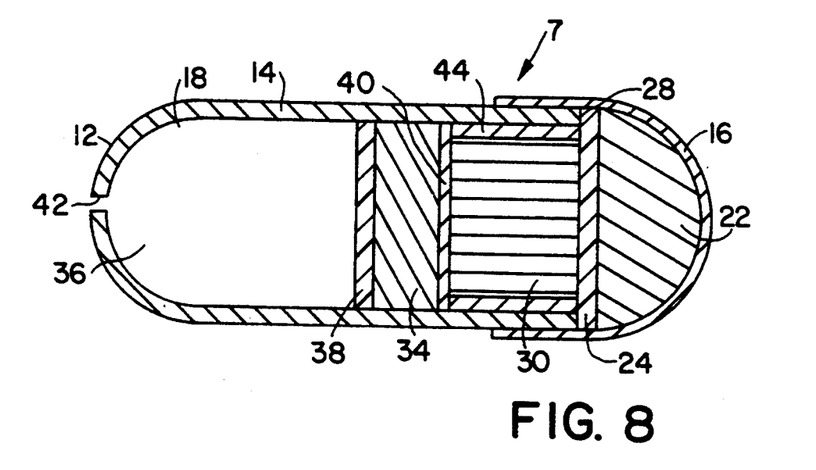
FIG. 8 is a cross-sectional view of a further embodiment of the present invention where one active agent is to be delivered in a controlled manner over a prolonged period of time and a second active agent is to be delivered after an initial delay period, the device being in closed form prior to placement in the environment of use.
Figure 9:
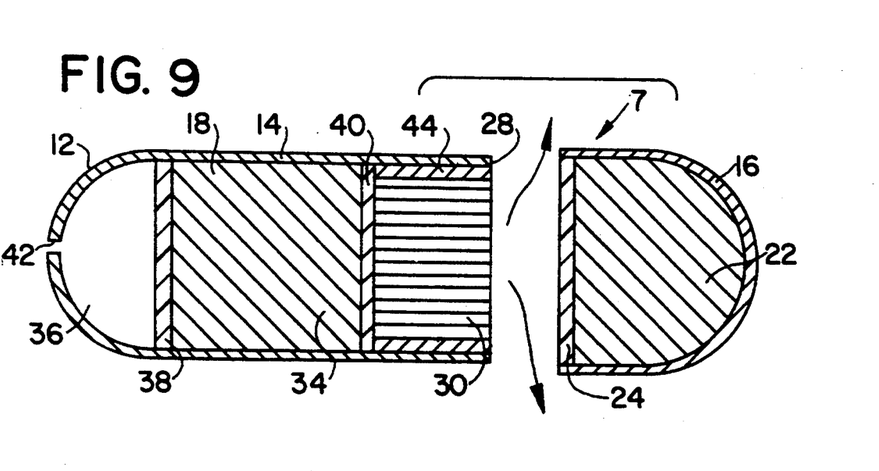
FIG. 9 is a cross-sectional view of the embodiment of FIG. 8, after activation, at a point in time when the device is opened to release the second active agent.
Figure 10:
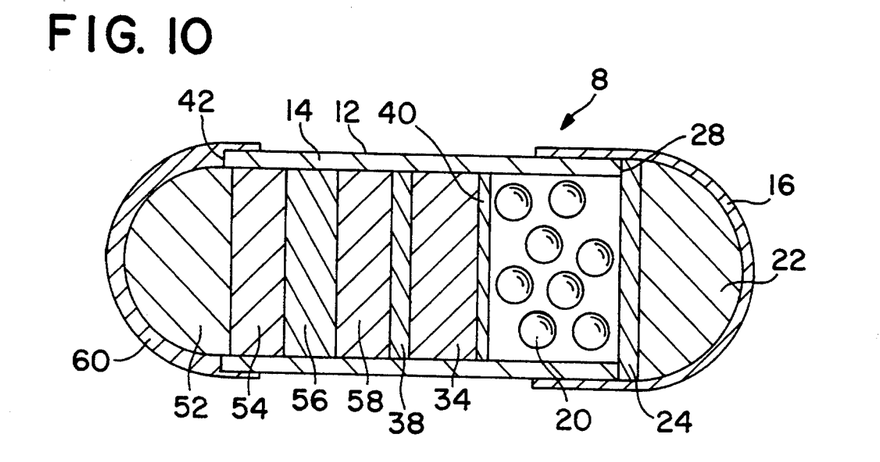
FIG. 10 is a cross-sectional view of another embodiment of the present invention, related to the embodiment of FIGS. 8 and 9.

FIG. 10 illustrates another embodiment of the device of the invention. As illustrated in this figure, dispensing device 8 is similar to dispensing device 7 of FIGS. 8 and 9, having a housing 12, a first wall section 14 with a ridge 28, a second wall section 16, an internal compartment 18 surrounded and defined by housing 12, first expansion means 34, second expansion means 22, first partition layer 38, second partition layer or push plate 24, barrier layer 40, and exit means 42. In dispensing device 7, the second active agent formulation is present as a plurality of active agent dosage forms as tiny pills 20 and the first active agent formulation is present as a plurality of active agent dosage forms as layers or tablets 52, 54, 56 and 58. Although four dosage layers are illustrated, the number is not critical and any number of dosage layers are included under the invention. Optionally, layers of a barrier material (not shown) may be placed between the agent dosage layers in alternating arrangement to provide a prolonged, repeating pulsed delivery. The exit means or passageway 42 may optionally be closed by an erodible material 60 such as, for example, microcrystalline wax or gelatin, for protecting the first active agent formulation prior to placement in the fluid environment, or there may optionally be present a retaining structure such as a screen or mesh or a ridge for retaining the dosage layers within the device until they are dispensed into the environment.

Figure 11:
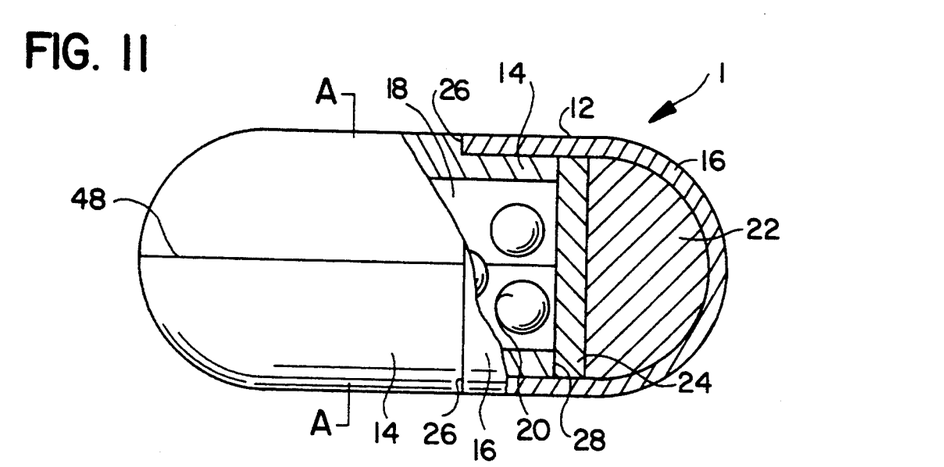
FIG. 11 is a partial cross-sectional view of another embodiment of the invention, having a first wall section of two longitudinal halves.

FIG. 11 illustrates, in partial cross-sectional view, a device 1 similar to the devices described in FIGS. 1–3 and having a housing 12 comprised of first wall section 14 and second wall section 16, an internal compartment 18 surrounded and defined by housing 12, a plurality of dosage forms 20, expansion means 22, push plate 24, receiving means 26 and ridge 28. FIG. 11 illustrates an alternative embodiment of the present invention where the first wall section 14 is comprised of two longitudinal halves which contact each other at longitudinal junction 48. It is to be noted that, while two longitudinal portions are presented by way of illustration, the invention is not limited thereto, and second wall section 14 may be comprised of from one to four or more longitudinal portions. The two longitudinal halves are held together by the pressure exerted on them by that portion of the open end of second wall section 16 that overlaps the open end of first wall section 14. When the two wall sections are separated by the action of the expansion means 22, the two longitudinal halves of first wall section 14 become free of the restraining pressure of second wall section 16 so that the two longitudinal halves can then separate from each other to provide additional exposure of active agent formulation to, or to aid in the release of the active agent formulation to the environment of use.

Figure 12A:
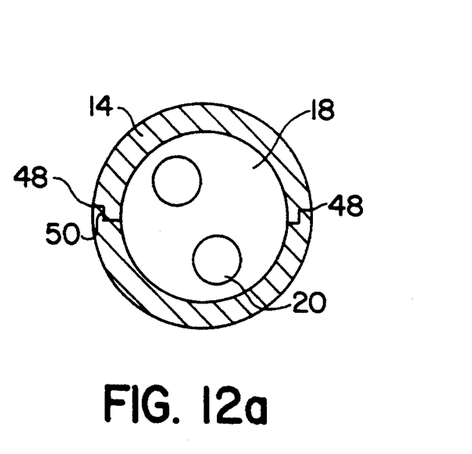
FIGS. 12a and 12b are views through the first wall section of the embodiment of FIG. 11 along line 11—11.
Figure 12B:
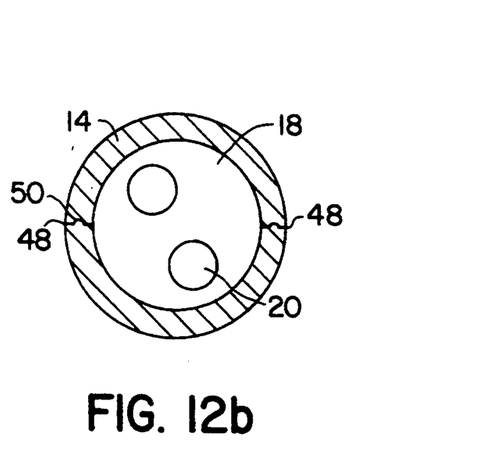

As illustrated in FIGS. 12a and 12b, which are section views along line 11—11 of device 1 of FIG. 11, the longitudinal walls of the two halves of first wall section 14 may be so shaped as to provide an interlocking means 50 between the two halves at the longitudinal junction 48. The interlocking means 50 may be, for example, an interlocking ridge that runs continuously along the length of the longitudinal walls of the two halves (FIG. 12a) or a plurality of interlocking concave and convex structures positioned at corresponding points along the longitudinal walls of the two halves (FIG. 12b). The interlocking means 50 provides an additional mechanism for maintaining the two longitudinal halves together while the device 1 is in closed form.

Figure 13:
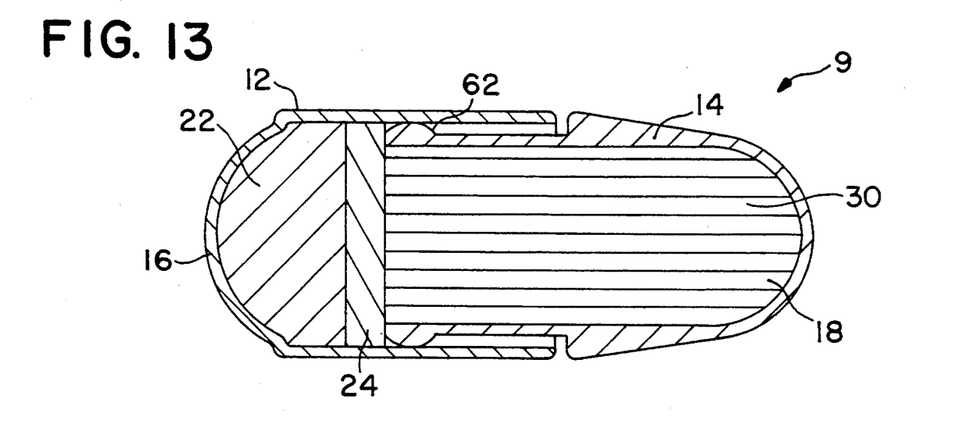
FIG. 13 is a cross-sectional view of yet another embodiment of the present invention.

FIG. 13 illustrates a device 9 similar to the devices described in FIGS. 1 and 2 and having a housing 12 having a first wall section 14 and a second wall section 16, an expansion means or driving member 22, a push plate 24, and an active agent formulation 30 which may be a solid, a semi-solid, a liquid or a thermo-responsive composition. Device 9 of FIG. 13 additionally has a protrusion 62 encircling the outer circumference of first wall section 14 at or near its open end. Protrusion 62 may be a continuous protrusion around the wall section or it may be a plurality of protrusions spaced at intervals around the wall section. Protrusion or protrusions 62 are in tight contact with the inner wall of second wall section 16, the protrusion or protrusions providing additional friction to increase the physical contact between and maintain the two wall sections of the device together until the point of separation of the sections. This further reduces the possibility of premature active agent release by unintended separation and additionally adds to the device's seal against fluid or other contamination.

For proper delivery of the active agent, it may be desirable in some instances for the dispensing device to deliver active agent to a particular environment of use. Thus, it may be necessary for the device to remain in a particular environment of use until such time as the agent formulation has been delivered or, alternatively, for the device to pass through one particular environment to another prior to delivering agent formulation. In such cases, additional elements are included in the device, or the device is designed in such a way to provide for such particular delivery. For example, when the environment of use is the rumen of a ruminant animal, a density element may be included in the dispensing device so that the device is weighted to remain within the rumen during the dispensing period. Density elements are known in the art and are discussed in, for example, U.S. Pat. No. 4,874,388. When the environment of use is the human stomach, it may be desirable for the device, for example, to have a low initial density or to include air in that portion of the internal compartment of the device that also contains the agent formulation. In this manner, the device will float on the surface of the stomach contents and remain in the stomach until the device opens to release the formulation. Where it is desirable, on the other hand, to delay the release of an active agent which, for example, is inactivated by the stomach contents or may cause nausea or bleeding by irritating the gastric mucosa so that delivery in the stomach is not desired, an enteric coating can be applied over at least that portion of the housing of the dispensing device that is comprised of a semipermeable membrane adjacent to the fluid-activated expansion means. Enteric coatings will remain intact in the stomach but will rapidly dissolve once they arrive at the small intestine, thereafter allowing fluid to be imbibed to activate the dispensing device. Enteric coatings are well known in the art and are discussed at, for example, Remington's Pharmaceutical Sciences, Mack Publishing Co., Easton, Penna.; and Polymers for Controlled Drug Delivery, Chapter 3, CRC Press, 1991.

The total delay time prior to separation of the dispensing device and delivery of the active agent formulation can be controlled by a number of means. For example, the rate of fluid imbibition into the expansion means can be controlled by the particular choice of semipermeable membrane. The rate of expansion of the expansion means can be controlled by the choice of composition of the expansion means. The distance of overlap between the open end portions of the first and second wall sections can determine the period of time required for the two sections to separate. Combinations of such means may be used. Such control means are known in the art and can be determined without undue experimentation.

The above description has been given for ease of understanding only. No unnecessary limitations should be understood therefrom, as modifications will be obvious to those skilled in the art.

The following examples are illustrative of the present invention. They are not to be construed as limitations of the scope of the invention. Variations and equivalents of these examples will be apparent to one skilled in the art in light of the present disclosure, the drawings and the claims herein.

EXAMPLE 1

A delivery device according to the invention was prepared as follows.

The osmotic engine portion of the device is a compressed bilayer tablet composed of a 150 mg polymeric osmotic formulation (expansion means) and a 50 mg wax-based barrier (push plate).

The polymeric osmotic formulation has a composition of 60 wt% polyethylene oxide (Polyox ®303, Union Carbide), 29 wt% sodium chloride, 5 wt% polyacrylic acid (Carbomer ®934P, B. F. Goodrich), 5 wt% hydroxypropylmethylcellulose E-5, and 1 wt% ferric oxide. During preparation, each of the above components was screened through a 40 mesh screen, and the sized components were added to a mixing vessel in the appropriate proportions. The dry components were mixed thoroughly for 10 minutes; then, SDA 3A ethanol was slowly added while mixing continued until a wet mass had formed. The wet mass was then screened through a 20 mesh screen, and the wet granules were allowed to air dry for 18 hours. After drying, the granules were passed once more through a 20 mesh screen.

The wax barrier has a composition of 95 wt% microcrystalline wax (MF-2JH Durawax®, Astor Wax Corp.) and 5 wt% gelatin (Type A, 275-300 bloom). During preparation, each component was screened through a 40 mesh screen before being added in the correct weight ratio to a mixing vessel. The dry materials were mixed thoroughly for 10 minutes; then, purified water was slowly added to the mixture while stirring continued. After a wet mass formed, the mixture was passed through a 20 mesh screen, and the granules were oven-dried at 40° C. for 24 hours. After the granules had dried, they were re-screened through a 20 mesh screen.

The osmotic formulation and the wax barrier formulation were compressed in a hydraulic or rotary press into a cylindrical bilayer tablet. The osmotic face of the tablet was convex, to conform to the shape of the delivery device, while the barrier face of the tablet was flat. Tabletting was conducted to produce a clean, distinct interface between the two layers.

To prepare the vessel portion (first wall section) of the device, 70 wt% cellulose acetate 320 and 30 wt% polypropylene glycol were thoroughly mixed together and were then added to the hopper of a screw extruder. The polymeric mixture was heated at 127° C. as it was extruded through the heated barrel of the extruder and into a mold for the vessel. The polymer mixture was allowed to cool after injection into the mold, after which the vessel was removed from the opened mold.

The cap portion (second wall section) of the device was prepared in the same manner as the vessel, the composition of the cap being 70 wt% cellulose acetate 320 and 30 wt% polypropylene glycol. The heated polymeric mixture was injected into a mold for the cap and allowed to cool, and the finished cap was then ejected.

To assemble the delivery device, the desired active agent formulation is placed into a completed vessel by manual or automated fill mechanisms. The osmotic engine bilayer tablet is placed into a completed cap with the convex osmotic layer pointed into the closed end of the cap and the barrier layer exposed toward the cap opening. The open end of the filled vessel is fitted inside the open end of the cap, and the two pieces are compressed together until cap, osmotic bilayer tablet and vessel fit together tightly.

EXAMPLE 2

A delivery device was prepared as in Example 1, except that the polymeric osmotic formulation was 130 mg. The assembled device was then coated with approx. 20 mg of a methacrylic acid copolymer enteric coat (Eudragit®L 100-55, Röhm Pharma).

EXAMPLE 3

A delivery device according to the present invention was prepared as follows.

The cap (second wall section) was formed by coating a gelatin capsule with a cellulose acetate-based membrane in the following manner. A coating solution composed of 5 wt% cellulose acetate 398 and polyethylene glycol 3350 (in a 95/5 weight ratio) in a solution of acetone/ethanol (in a 90/10 weight ratio) was sprayed onto a size "0" clear gelatin capsule in a Wurster coater. The capsule was coated to a membrane thickness of 3-4 mil. The capsule was then dried in a 50° C. oven to remove residual solvent, after which the two parts of the capsule were separated with their respective membrane covering intact. The short segment of the coated capsule was retained as the required cap, while the long segment was discarded.

The vessel (first wall section) was formed by machining a cylindrical container with one open end from polycarbonate polymer. The machined dimensions were such that the open end of the vessel will fit snugly within the coated gelatin cap.

To assemble the device, following the procedure of Example 1, the osmotic engine bilayer tablet from Example 1 was placed in the cap portion, the desired active agent formulation was placed in the vessel portion, the open end of the vessel portion was fitted into the open end of the cap portion, and the two pieces were compressed together to obtain a tight fit.

Another device was prepared following the above procedures, except that during manufacture of the cap portion, the gelatin capsule was coated with a cellulose acetate/polyethylene glycol membrane of 8-9 mil thickness.

EXAMPLE 4

Delivery devices were prepared as in Example 3, except that the weight ratio of cellulose acetate to polyethylene glycol in the membrane covering the cap was 80/20.

EXAMPLE 5

Nine devices from Example 1, but not containing any active agent formulation, were assembled and placed in artificial intestinal fluid (USP XIX, intestinal fluid, simulated, TS; modified herein by not including enzymes) in a shaker bath at 37° C. Marbles were also added to the fluid to provide abrasion with the devices, simulating an intestinal environment. The devices were observed to determine when the cap and vessel portions separated from each other. The resulting average release point for the devices was at 3.84 hours (SD=0.18 hr).

EXAMPLE 6

Two enteric-coated devices from Example 2, but not containing any active agent formulation, were assembled and placed in artificial gastric fluid (USP XIX, gastric fluid, simulated, TS; modified herein by not including enzymes) for 2 hours, after which they were removed from the gastric fluid and placed in artificial intestinal fluid. The devices were observed in the intestinal fluid to determine when the cap and vessel portions separated. The resulting average release point for the two devices was at 6.33 hours.

EXAMPLE 7

Four devices from Example 3 having a cap membrane thickness of 3-4 mil and containing cardizem pellets as the active agent formulation were placed in artificial intestinal fluid and observed for separation. The devices separated and the cardizem pellets were released to the fluid environment at an average time of about 1.4 hours after placement in the fluid.

In the same manner, three devices from Example 3 having a cap membrane thickness of 8-9 mil and containing cardizem pellets were placed in the artificial intestinal fluid environment. The devices separated and the cardizem pellets were released at an average time of about 7.1 hours after placement.

EXAMPLE 8

Five devices from Example 3 having a cap membrane thickness of 8-9 mil and containing cimetidine granules as the active agent formulation were placed in artificial intestinal fluid and observed for separation. The devices separated and the cimetidine granules were released to the fluid environment at an average time of about 6.4 hours after placement in the fluid.

EXAMPLE 9

A delivery device according to the present invention containing calcitonin, and similar to that illustrated in FIG. 1, was prepared as follows.

The cap (second wall section) was formed by coating a size "0" gelatin capsule, according to the procedures of Example 3, with 54 mg of a semipermeable membrane comprised of 60 wt% cellulose acetate 398-10 and 40 wt% hydroxypropylcellulose (Klucel®EF), the short segment of the coated capsule being retained as the required cap.

The vessel (first wall section) for containing the active agent unit was formed by machining a cylindrical container with one open end from ethylene vinyl acetate copolymer, having 9% vinyl acetate. The machined dimensions were such that the open end of the drug vessel will fit snugly within the coated gelatin cap and the inside dimensions will contain 110 mg of a calcitonin formulation.

The calcitonin formulation has a composition of 0.91 wt% calcitonin, 0.18 wt% sodium citrate, 0.28 wt% anhydrous citric acid, and 98.63 wt% mannitol.

An osmotic engine bilayer tablet was made following the procedures of Example 1, except that the polymeric osmotic formulation has a composition of 59.65 wt% Polyox®303 and in addition to the other ingredients also has 0.25 wt% magnesium stearate and 0.10 wt% BHT, and the wax barrier has a composition of 90 wt% microcrystalline wax (MF-2JH Durawax®) and 10 wt% hydroxypropylcellulose (Klucel®HF). The resulting bilayer tablet contained 150 mg of the osmotic formulation and 60 mg of the wax barrier formulation.

To assemble the device, following the procedure of Example 1, the osmotic engine bilayer tablet was placed in the cap, the calcitonin formulation (110 mg) was placed in the active agent vessel, the open end of the vessel was fitted into the open end of the cap, and the two pieces were compressed together to obtain a tight fit.

EXAMPLE 10

Figure 14:
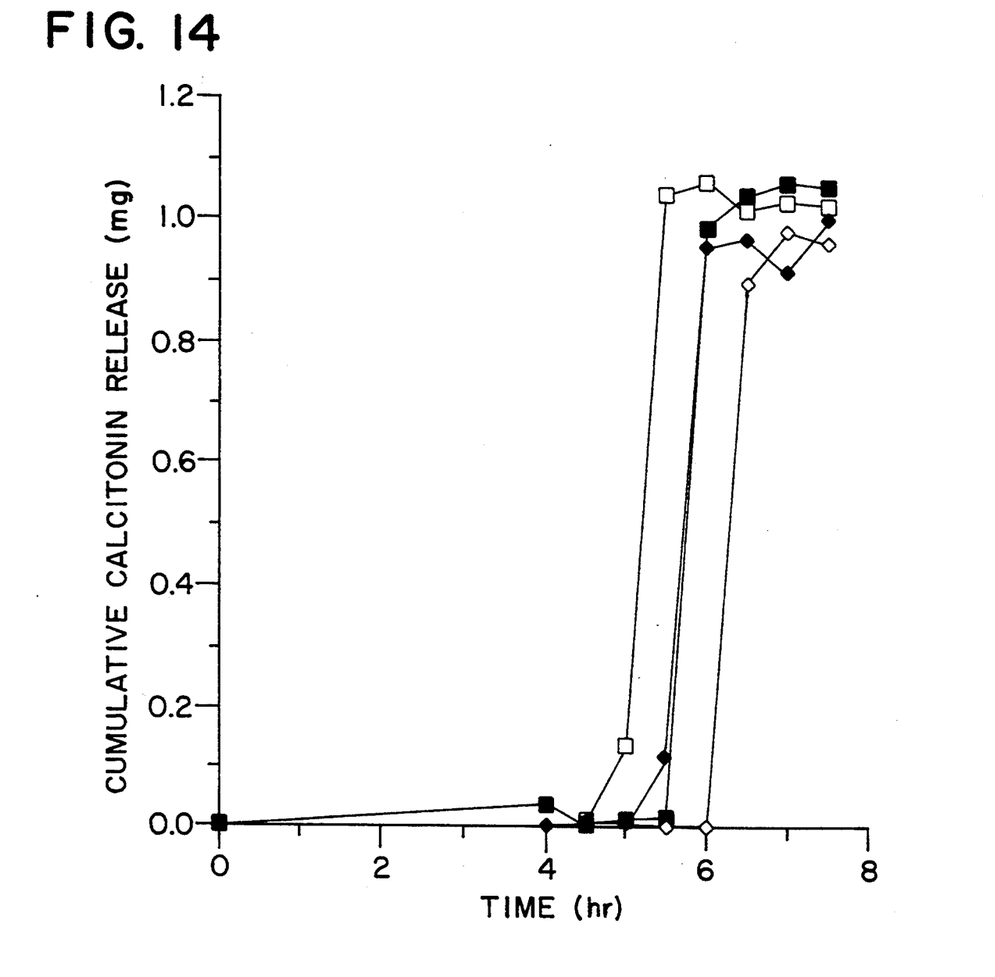
FIG. 14 shows the release profile of calcitonin from a device of the present invention.

Four delivery devices similar to the device of Example 9, each containing 1 mg of calcitonin and having a cap membrane thickness of approx. 6 mils, were tested for release of calcitonin using the USP paddle method (at 150 rpm). The devices were placed in 500 mL of pH 4 solution with 0.1% bovine albumin and stirred. The devices were observed to determine when the cap and drug vessel separated from each other, and the solution was then tested for presence of calcitonin to confirm the drug release time and the duration of release. The results are shown in FIG. 14 and indicate that each device released its content completely after 4 to 6 hours and over a short duration of time of less than half an hour.

EXAMPLE 11

The current route of administration of influenza antigens is by injection, which is inconvenient and painful for patients. In addition, these injectable influenza virus vaccines afford incomplete protection, estimated in various studies at 30-90%. Evidence has indicated that protection against influenza correlates better with the presence of antibodies at the mucosal surfaces than with serum antibodies (see, Liew et. al., Eur. J. Immunol. (1984), 14, 350–356; Wladman et. al., Am. J. Med. Sci. (1986), 292, 367–371; Murphy and Clemens, Curr. Top. Microbiol. Immunol. (1989), 146, 107–116; Renegar and Samll, J. Immunol. (1991), 146, 1972–1978; and Renegar and Samll, J. Virol. (1991), 65, 2146–2148). The Peyer's patches are located in the lower jejunum and ileum of the intestine. It is well known that the Peyer's patches are an important part of the body's defense against bacterial infection. Thus, an oral delivery system will have high efficacy of immunization if the system can dispense the vaccine formulation right to the Peyer's patches with the antigen protected from degradation or inactivation while the system is passing through the stomach and upper part of the small intestine. A device according to the present invention can deliver such a drug or protein as a bolus at a predetermined time. Due to significant variations of gastric residence time, an enteric coating on the semipermeable membrane of the osmotic engine cap (second wall section) is required in order to avoid premature opening in the stomach during the time of gastric residence.

A device for delivery of influenza antigen to the Peyer's patches was prepared generally following the procedures of Example 1 and as described below.

The barrier layer (push plate) material was prepared by screening each of hydroxypropyl methyl cellulose E-5 ("HPMC") and stearic acid through a 40mesh screen. The HPMC (5 wt%) and stearic acid 95 wt% were blended in a mixer for 10 min., after which ethanol was slowly added to the dry blend until a wet mass was formed. The weight ratio of ethanol to the dry blend was 0.273. The wet mass was passed through a 20-mesh screen, spread out and dried at RT overnight. The dried granules were again passed through a 20-mesh screen.

To prepare the osmotic engine formulation, 58.75 wt% sodium carboxymethylcellulose, 30 wt% sodium chloride (sized using a 21-mesh screen), 5 wt% HPMC E-5, and 1 wt% red ferric oxide were blended together. In a separate container, the granulating solution was prepared by dissolving 5 wt% hydroxypropylcellulose EF in purified water. The granulating solution was then sprayed onto the fluidized powders until all of the solution was applied and the powders were granular. Fluidizing was continued for a time, after which the granules were passed through a 16-mesh screen. Magnesium stearate (0.25 wt%) was then added to the granules and blended in.

An osmotic engine bilayer tablet was prepared by first adding 200 mg of the osmotic engine formulation to a 9/32 inch punch (lower punch=modified ball, upper punch=flat) and tamped, then adding 50 mg of the barrier layer granules onto the tamped osmotic layer granules. The materials were compressed under a force of about 1 metric ton into a contacting laminated core.

The cap (second wall section) was prepared by separating a clear, size "0" gelatin capsule into two segments. An osmotic engine bilayer tablet was then pushed all the way into the bottom of the shorter segment of the gelatin capsule. The cap assembly was coated with a semipermeable membrane having a composition of 75% cellulose acetate 398-10 and 25% polyethylene glycol 3350. The membrane composition was dissolved in acetone/methanol (80/20, wt/wt) mixed solvent to make a 4% solid solution, which was sprayed onto the assemblies to a weight of 11 mg. The membrane-coated cap assembly was then coated with an enteric composition of 10% triacetin and 90% of either Eudragit L-100 (dissolves at pH 6 or above) or Eudragit L100-55 (dissolves at pH 5.5 or above). The enteric coating composition was dissolved in solvent to make a solution of 4% solute, and the solution was sprayed onto the assemblies to a weight of 5.7 mg. After enteric coating, the cap was dried.

A drug vessel (first wall section) was fabricated by injection molding ethylene vinyl acetate copolymer (9% vinyl acetate) into the desired configuration having a height of 0.605in and an inside diameter of 0.245in and with a weight of 185.2 mg.

To assemble the final device, 55.4 mg of a lyophilized formulation with 37.5 μg influenza antigen was placed into the drug vessel, the open end of the vessel was fitted into the open end of the cap, and the two pieces were compressed together to obtain a tight fit.

EXAMPLE 12

The opening time of the device of Example 11 was determined by placing devices prepared as in Example 11, but without any influenza antigen in the drug vessel, into a USP shaker bath containing 700 mL of medium having various pHs. The bath was at 37° C. and 50 rpm. Each device was mounted on a sample holder made of copper to prevent the device from floating during measurement. The opening time was defined as the time when the osmotic engine cap separated from the drug vessel, and was observed visually. Both Eudragit L100 coated and Eudragit L100-55 coated devices were tested.

The devices all opened at between 1 and 2 hours at pH 6 and in artificial intestinal fluid (pH 7.4). In contrast, the opening time was between 8 and 9 hours at pH 3 and greater than 12 hours in artificial gastric fluid (pH 1.4).

EXAMPLE 13

To measure the delay and opening times and content delivery of the device of Example 11, devices were prepared as described in Example 11 except that influenza antigen was replaced with a blue release marker. The release marker was a granulation comprising 4% Reactive Blue dye, 5% polyvinyl pyrrolidone K29-32, and 91% lactose monohydrate. All devices had a Eudragit L-100 enteric coating.

The opening time and content delivery were measured in 20 mL of a medium at 37° C. using a shaker bath. To keep the devices from floating during measurements, the vessel of each device was wrapped ten times with 20 mildiameter wire made of annealed stainless steel. To measure the release profile, 1.0 mL aliquots were withdrawn one hour after the device was placed into artificial intestinal fluid and every 15 minutes thereafter until all the granules in the vessel had dissolved. One mL of AIF was added into the container after each withdrawal. To minimize the uptake of water by the osmotic polymer after the device has opened, the osmotic cap was removed immediately following separation. The blue dye concentration of the aliquots was measured by a spectrophotometer at a wavelength of 598 nm.

Figure 15:
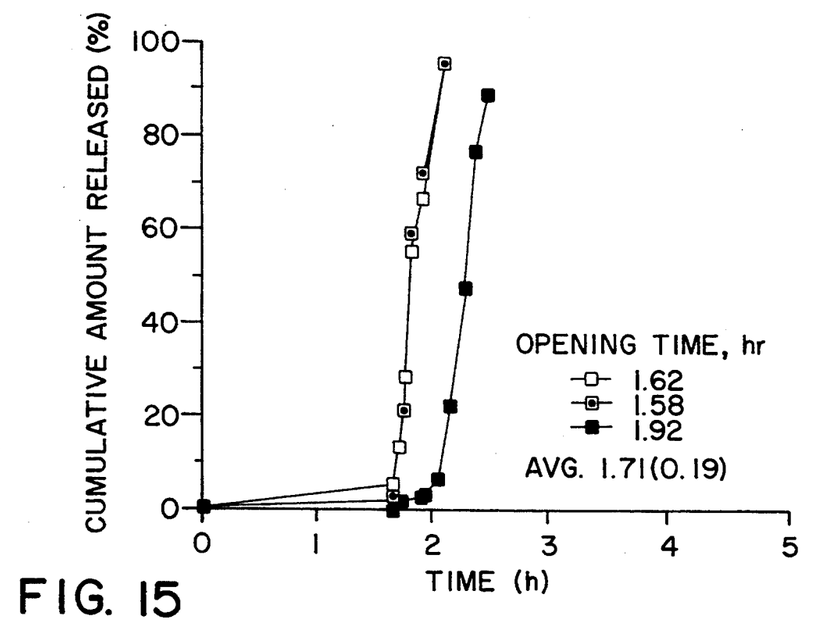
FIG. 15 shows the release profile of a release marker from a device of the present invention, with enteric coating, into artificial intestinal fluid following 2 hours presoaking in artificial gastric fluid.
Figure 16:
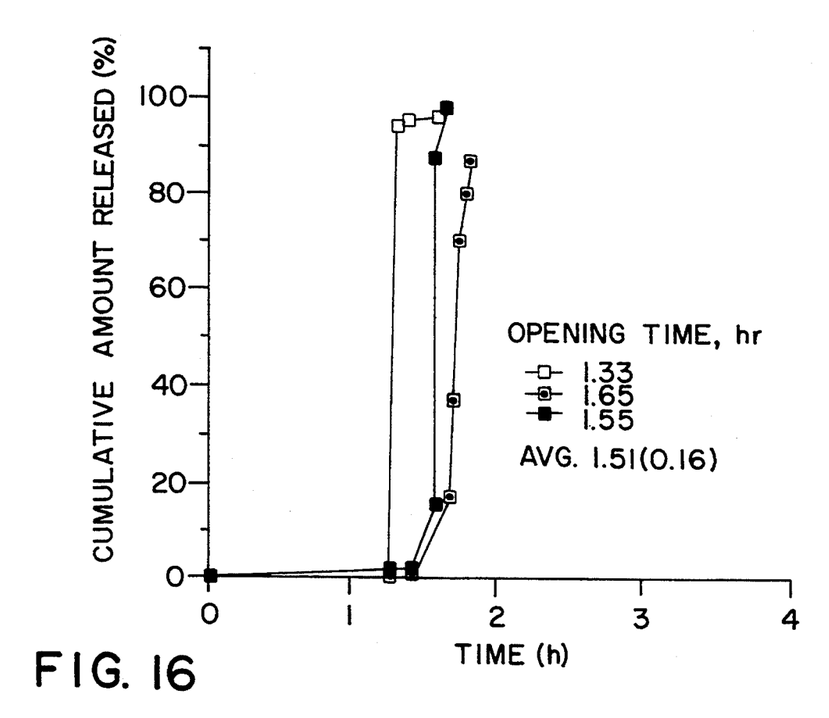
FIG. 16 shows the release profile of a release marker from a device of the present invention, with enteric coating, into artificial intestinal fluid.

The release profiles of the blue dye granules are shown in FIG. 15 (with 2 hours presoaking in artificial gastric fluid) and FIG. 16 (no presoaking). The Figures show that in both instances the devices opened between 1 and 2 hours after placement in the AIF and that dye release occurred substantially immediately after the devices had opened and had completed release within 0.5 hour or less.

EXAMPLE 14

Following the procedures of Example 11, a device was prepared that was the same as the device of Example 11, except that it contained 109 mg of lyophilized formulation with 112 μg influenza antigen. The device had a Eudragit L-100 enteric coating.

In the same manner, a similar device was prepared, except that it contained 180 mg of lyophilized formulation having 337.5 μg influenza antigen.

EXAMPLE 15

A device for delivering human growth hormone was prepared following the procedures of Example 11, except that the cap (second wall section) was coated with a semipermeable membrane having a composition of 90% cellulose acetate 398-10 and 10% polyethylene glycol 3350, with the membrane weight being about 35 mg; the cap did not have an enteric coating; and 400 mg of solid human growth hormone (hGH) formulation was loaded in the drug vessel (first wall section).

EXAMPLE 16

A device for delivering flutamide in two pulses, one as an immediate delivery and the second as a delayed delivery, is prepared as follows.

Following the procedures of Example 1, a device is made having a configuration basically like that of the device in FIG. 5, except that one of the internal compartments, containing a first flutamide formulation, does not include a push plate and the semipermeable cap covering the first flutamide formulation is replaced with a dissolvable gelatin cap, so that the first or loading dose flutamide formulation will be exposed to the fluid environment shortly after placement in the environment to provide a first, initial pulse of flutamide delivery. The other of the two internal compartments contains a second flutamide formulation and a push plate and has a semipermeable cap for providing a delayed delivery of the second flutamide formulation at a time after placement in the environment and after delivery of the first, loading dose flutamide formulation to give a second pulse of flutamide.

This invention has been described in detail with particular reference to certain preferred embodiments thereof, but it will be understood that variations and modifications can be effected within the spirit and scope of the invention.

What is claimed is:

1. A dispensing device for providing a pulsed delivery of at least one active agent formulation to a fluid-containing environment of use, which device comprises a plurality of nested capsules, each succeeding capsule being nested within the preceding capsule, each capsule comprising a housing having a first wall section and a second wall section in reversibly sliding telescopic arrangement, which wall sections are assembled together to define an internal compartment which contains an active agent formulation and expansion means and the next succeeding capsule, if any, wherein at least one of said wall sections of each capsule is, at least in part, permeable to fluid in the environment of use, the arrangement being such that in said environment of use fluid enters into the internal compartment of the first outer capsule and interacts with said expansion means, thereby causing the expansion means to expand and to exert a separating force on the wall sections of said first capsule, whereby, after a period of time, said wall sections of said first capsule are disassembled from each other thereby exposing the contents of the said internal compartment to the said environment of use and allowing delivery of said active agent formulation therein and the ingress of fluid into the next succeeding capsule, thereby to provide the said pulsed delivery of active agent.

* * * * *